United States Patent [19]

Scher et al.

[11] 4,107,509

[45] Aug. 15, 1978

[54] APPARATUS FOR TREATING BODY MEMBERS WITH HEAT AND MOISTURE

[75] Inventors: Victor H. Scher, Fort Lauderdale, Fla.; Theodore A. Fox, Winnetka; Philip A. Sandford, Highland Park, both of Ill.

[73] Assignee: Northern Electric Company, Chicago, Ill.

[21] Appl. No.: 775,086

[22] Filed: Mar. 7, 1977

[51] Int. Cl.² ............................................. H05B 1/00
[52] U.S. Cl. ................................... 219/211; 128/379; 128/381; 128/402; 219/527; 219/529
[58] Field of Search ....................... 219/211, 527–529, 219/549; 126/204; 128/379, 381, 382, 399, 402

[56] References Cited

U.S. PATENT DOCUMENTS

| | | | |
|---|---|---|---|
| 2,339,409 | 1/1944 | Joy et al. | 219/528 X |
| 2,590,212 | 3/1952 | Samuels | 219/527 X |
| 2,609,479 | 9/1952 | Lowe | 219/529 |
| 2,769,892 | 11/1956 | Collins | 219/528 X |
| 3,673,485 | 11/1971 | Price | 219/527 X |
| 4,042,803 | 8/1977 | Bickford | 219/211 |

Primary Examiner—C. L. Albritton
Attorney, Agent, or Firm—George R. Clark; Neil M. Rose; Clifford A. Dean

[57] ABSTRACT

Apparatus for treating portions of the arms or legs of a human body with heat and moisture by means of a moisture-resistant heating pad retained in a cylindrical configuration by means of a fabric enclosure having means to receive the heating pad and retain it in its circular configuration in close proximity to the body member being treated. A suitable moisture source is provided in the form of a pad positioned in the enclosing material.

8 Claims, 8 Drawing Figures

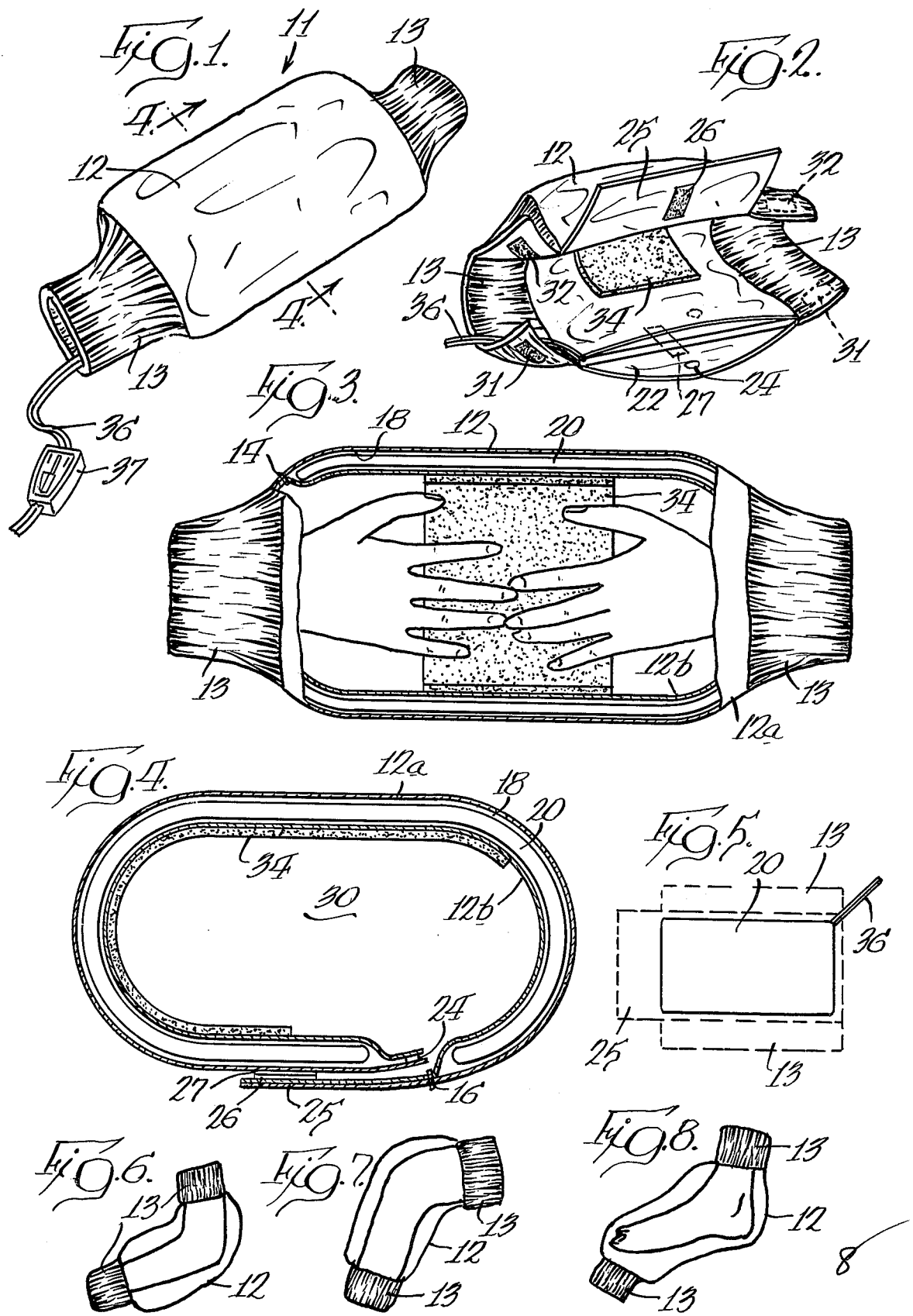

APPARATUS FOR TREATING BODY MEMBERS WITH HEAT AND MOISTURE

BACKGROUND OF THE INVENTION

The present invention relates to apparatus for treating portions of the human body such as the feet, elbows, knees and hands with heat and moisture.

There are many situations in which doctors recommend for their patients the application of heat and moisture to a portion of their body. Often, this treatment is for simple muscular discomfort or, perhaps, more chronic afflictions such as arthritis. While such treatments may or may not have any curative effects, at least it is recognized that such treatments soothe or reduce the pain in the area so treated.

The typical heating pad which has been available for many years is an effective source of low temperature heat for application to the human body. However, the heating pad is generally flat in shape and ill-equipped to surround an afflicted body member such as a leg or arm. There have been straps and other means provided on heating pads to enable the user to wrap it around the body or the extremities. Because of the versatility of the pads provided with such straps, they are not effective in providing a suitable enclosure for any portion of the body. In an effort to provide a more complete enclosure for portions of the body such as the hands, specially heated devices such as gloves or mittens have been provided. Noted in this connection is Maxwell et al. U.S. Pat. No. 3,292,628 and Joy et al. U.S. Pat. No. 2,298,298. Although mittens of the type disclosed in the Maxwell et al and Joy et al patents are effective in heating hands, they are expensive to fabricate, difficult to seal from a moisture standpoint and lack versatility since they are limited to use in heating the hands. Other disclosures of interest with respect to heating the face are the British patent to Nightingale, No. 1,038,891, and the French patent to Thermobelle, No. 1,511,723.

In connection with the application of moisture along with the heat, it has been known to utilize a moisture-resistant pad. The patent to McDonald, U.S. Pat. No. 2,032,294, is noted in this connection. A pad of fibrous material is soaked in water to permit it to absorb water which will later be driven off as heat is applied to create the damp, heated environment which is desirable in connection with this therapeutic treatment. The use of the moisture pad in close proximity with the heat pad requires much care in order that the user not be electrocuted by the electricity used in connection with the heating pad. A sealed envelope of waterproof or moisture-resistant material is conventionally used to enclose the electric heating element of the pad. The difficulties of adequately sealing an envelope of complex configuration such as is shown in the Maxwell et al. and Joy et al. patents can readily be appreciated.

BRIEF DESCRIPTION OF THE INVENTION

The invention involves the use of an electric heating pad having a generally rectangular configuration and being provided with a sealed envelope made of a flexible plastic material with the power cord for the pad issuing from one corner, the portion of the envelope through which the power cord extends being sealed to the cord itself.

A fabric envelope having tubular configuration providing a pocket within which the heating pad is received is designed to be rolled into a cylindrical configuration with means provided on the envelope to retain it in the rolled configuration. At the ends of the envelope, there are provided elastic cuffs which open to permit unrolling of the envelope but may be closed by means of fasteners to form entrance seals through which the arms or legs may extend into the interior of the rolled, cylindrical envelope. A moisture pad is positioned within the envelope to create the moist heat for therapeutic treatment of the body parts positioned within the apparatus.

It is, therefore, an object of the present invention to provide improved apparatus for the treatment of body extremities with heat and moisture.

It is a further object of the present invention to provide a therapeutic muff including a removable heating pad and moisture pad enclosed within a cylindrical fabric member which may be opened for the purpose of inserting the body members.

Still another object of the present invention is to provide therapeutic apparatus including a moisture-sealed heating pad and a cloth retainer having an envelope to receive the heating pad and being formable to an enclosure in order to receive the hands or feet to be treated with heat and moisture.

It is another object of the present invention to provide a fabric envelope for supporting a moisture-sealed heating pad in a cylindrical position with cuff members formed on the ends of the fabric member to provide an enclosure within which the hands or feet may be treated with heat and moisture.

Further objects and advantages of the present invention will become apparent as the following description proceeds and the features of novelty which characterize the invention will be pointed out with particularity in the claims annexed to and forming a part of this application.

BRIEF DESCRIPTION OF THE DRAWINGS

For a better understanding of the present invention, reference may be had to the accompanying drawings in which:

FIG. 1 is a perspective view of the apparatus for treating body members with heat and moisture.

FIG. 2 is a perspective view similar to FIG. 1 but showing the apparatus in an opened condition suitable for insertion of a body member to be treated.

FIG. 3 is an enlarged view of the apparatus of FIG. 1 showing a portion of the side wall cut away to illustrate the position the hands would typically assume within the apparatus.

FIG. 4 is a sectional view taken on line 4—4 of FIG. 1.

FIG. 5 is a view of the moisture-resistant heating pad which is shown in an unrolled position with the outline of the supporting fabric member shown in dotted lines.

FIG. 6 is a view similar to FIG. 3, however, showing the position of an elbow within the apparatus.

FIG. 7 is a view similar to FIG. 6 but showing a knee within the apparatus.

FIG. 8 is similar to FIGS. 6 and 7 but showing a foot within the apparatus.

Referring to the drawings, there is shown in FIG. 1 apparatus for treating body members with heat and moisture designated generally by reference numeral 11. Because of its general similarity in outward appearance to a muff for protecting the hands from the cold, the device will be referred to herein as a therapeutic muff.

The therapeutic muff 11 is formed of a central, cylindrical portion 12 to which are attached the cuff portions 13. The central portion 12 is formed by an outer rectangular panel or wall 12a and an inner rectangular panel or wall 12b. The edges of the rectangular panels 12a and 12b are secured together by stitching which also secures the cuffs 13 to the cylindrical portion 12. This stitching, as best shown at 14 in FIG. 3, secures the panels 12a and 12b together around the periphery of the therapeutic muff 11 as shown in FIGS. 3 and 4 and, at the same time, secures the cuff portions 13 thereto, the inner edges of the cuff portions 13 being positioned between the edges of panels 12a and 12b.

At one end of the stitching 14, there is provided a transverse seam 16 as best shown in FIG. 4. The stitching forming the transverse seam 16 cooperates with the stitching 14 to form an envelope having a chamber 18 within the cylindrical portion 12. This chamber 18, as is best illustrated in FIG. 4, encloses a rectangular, moisture-resistant heating pad 20. The chamber 18 is closed at one end by seam 16 and is provided with an opening 22 at the other end into which the heating pad 20 may be inserted into the central portion 12 of the therapeutic muff 11.

In order to retain the heating pad within the envelope formed by the panels 12a and 12b, there is provided a snap fastener 24 at the mouth 22. The snap fastener permits the ends of the outer panel 12a and the inner panel 12b to be secured together as shown in FIG. 4, thereby preventing the pad 20 from sliding out of the chamber 18.

The portions of the panels 12a and 12b extending beyond the seam 16 and chamber 18 provide a flap 25 which is formed by the adjacent edges of the panels being sewn together. Positioned on the flap 25 is a Velcro retainer 26, which is adapted to engage a complementary retainer 27 mounted on the wall 12a of the central portion 12 as best shown in FIG. 4. Thus, when the Velcro retainers 26 and 27 are engaged, the central portion 12 is held in a tubular form which may be generally cylindrical or oval, as shown in FIG. 4. This tubular form provides a treatment area 30 within which the hands or other portions of the human extremities may be positioned for treatment.

The cuffs 13 are formed of a ribbed, elastic material commonly used as the wrist engaging portions of jackets designed for wear in cold weather. The cuffs 13 differ from the cuffs found in such jackets, however, since they are not continuous, as is evident from FIG. 2. With the disengagement of the Velcro retainers 26 and 27, the therapeutic muff 11 may be opened to a flat configuration so that the muff may then be wrapped around the knee or elbow, as shown in FIGS. 6 or 7, or placed around the feet or hands, as shown in FIGS. 3 and 8. To form the enclosure 30 within which the body extremities are positioned for treatment, the central portion 12 is wrapped, as shown in FIG. 4, with the Velcro retainers 26 and 27 being engaged. In addition, the cuffs 13 are formed with Velcro retainers 31 and 32 which permit the cuffs to be wrapped and formed into generally cylindrical portions which might surround the wrist, arms or portions of the legs. With the Velcro retainers 26, 27, 31 and 32 engaged, there is provided a reasonably tight enclosure within which the heat and moisture treatment may take place.

Within the enclosure 30, there is positioned a rectangular pad 34 which is made of an open-celled or sponge-like matter capable of absorbing large quantities of water. In use, the pad 34 is saturated with water and inserted within the central portion 12 when the therapeutic muff 11 is in the open position, as shown in FIG. 2. The heating pad 20 is provided with a power cord 36 which extends out through the opening 22 and through the cuff 13 to a position where it can be plugged into a suitable power outlet. A switch 37 is provided to control the flow of electricity to the pad 20. When the heating pad 20 is energized, the heat produced therein tends to drive the moisture from the pad 34, thereby creating a warm and moist environment within the treatment area 30. The cuffs 13 tend to prevent leakage of the moist air from within the area 30 and, therefore, extend the time before which the pad 34 dries out and must be remoisturized.

The fabric envelope which makes up the central portion 12 of the therapeutic muff 11 provides a simple, inexpensive means of forming an enclosed treatment area within which heat and moisture may be applied to extremities of the human body. Although the central portion 12 is formed of an inexpensive, porous material, it retains the heating pad 20 with its moisture resistant cover in a tubular form so that, in effect, the heating pad itself actually forms the walls around the treatment area 30 which limits or prevents the moisture from passing outwardly therefrom. The fact that the heating pad 20 is simply insertable within the chamber 18 through opening 20 provides an arrangement in which the heating pad 20 may readily be disassembled from the rest of the therapeutic muff so that the fabric portions may be easily laundered. This aspect becomes important when one considers the need for use of medicaments on the portions being treated within the muff.

While there has been shown and described a particular embodiment of the present invention, it will be apparent to those skilled in the art that various changes and modifications may be made without departing from the invention in its broader aspects, and it is, therefore, contemplated in the appended claims to cover all such changes and modifications as fall within the true spirit and scope of the present invention.

What is claimed as new and desired to be secured by Letters Patent of the United States is:

1. Apparatus for treating the body with heat and moisture comprising a rectangularly-shaped electric heating pad having a waterproof covering over the entire pad with the power cord extending from one corner thereof, a double-walled fabric member forming a pocket within which said heating pad is removably received, said heating pad being coextensive with said pocket formed in said member, said member having a flap and retaining means on said flap and said pocket to hold said member in a tubular configuration with the ends of said pad being in closely spaced relation, cuffs of elastic material, each of which is attached along an edge to said member, said cuffs being positioned at opposite ends of said tubular configuration of said member, said cuffs extending the length of said pocket and each having retaining means to secure it in a closed tubular configuration to form with said member a chamber for treatment of body members.

2. The combination of claim 1 wherein said pocket has an opening thereto at an edge of said member remote from said flap, snap fastening means on the opposed walls of said pocket at said opening to secure said heating pad against displacement from said pocket.

3. The combination of claim 1 wherein said chamber is provided with an elongated pad having high liquid absorption characteristics which, when saturated with water, provides moisture to said chamber when said heating pad is energized.

4. The combination of claim 2 wherein said power cord extends through said pocket opening and through the tubular configurationed cuff adjacent the corner of the heating pad from which said cord extends.

5. Apparatus for treating the body with heat and moisture comprising an open-ended tubular fabric member, said member being made of a porous, woven material and having double walls forming a pocket extending completely about said tubular member, said pocket having a closed end and an open end in closely spaced relation, said spaced ends extending lengthwise of said tubular member, a flap on said closed end to detachably secure said ends in said closely spaced relation, an electric heating pad with a waterproof cover removably received in said pocket and having a power cord extending from said pocket opening, said heating pad being coextensive with said pocket and forming a moisture-proof, tubular member defining in part a chamber within which portions of the body may be treated with heat and moisture, and elastic cuffs secured at their edges to the double-walled portions defining said pocket to partially close the open ends of said tubular member.

6. The combination of claim 5 wherein said cuffs are elongated elastic members, each secured along one edge to said tubular member and each having complementary attachment means at their ends to detachably secure together the opposite ends of each of said cuffs to form tubular extensions on the opposite ends of said tubular member.

7. The combination of claim 6 wherein said member is formed of two rectangular, coextensive fabric walls secured together continuously along their edges except at said pocket opening, a flap formed in said tubular member at the closed end of said pocket and overlapping the end of said pocket having said opening, complementary assembly means on said flap and said pocket to detachably secure said flap to said pocket to retain said member in its tubular configuration.

8. The combination of claim 2 wherein said pocket opening is provided with a snap fastener to secure said heating pad against displacement from said pocket, and a moisture-absorbent pad positioned within said chamber.

* * * * *